United States Patent [19]

Gotchel et al.

[11] 4,311,037
[45] Jan. 19, 1982

[54] WEB PERMEABILITY TESTER

[75] Inventors: Joel P. Gotchel, Glen Mills; Rudolf Neuenschwander, Swarthmore, both of Pa.

[73] Assignee: Scott Paper Company, Philadelphia, Pa.

[21] Appl. No.: 131,803

[22] Filed: Mar. 19, 1980

[51] Int. Cl.³ ............................................ G01N 15/08
[52] U.S. Cl. ......................................... 73/38; 73/37.7
[58] Field of Search ........................... 73/38, 37.7, 159

[56] References Cited

U.S. PATENT DOCUMENTS

| | | | |
|---|---|---|---|
| 2,861,451 | 11/1958 | Emmons | 73/38 |
| 3,115,037 | 12/1963 | Forrester | 73/37.7 X |
| 3,371,518 | 3/1968 | Keyes | 73/38 |
| 3,466,925 | 9/1969 | Ziegenhagen et al. | 73/38 |
| 3,475,956 | 11/1969 | Langlois et al. | 73/37.7 X |
| 4,246,775 | 1/1981 | Stultz | 73/38 |

FOREIGN PATENT DOCUMENTS 980058 1/1965 United Kingdom ................... 73/38

Primary Examiner—Charles A. Ruehl
Assistant Examiner—Joseph W. Roskos
Attorney, Agent, or Firm—Joseph H. Yamaoka; John W. Kane, Jr.

[57] ABSTRACT

An apparatus for testing the permeability of porous web materials. The porous web 12 is placed against a surface of a test head 10 of the apparatus. The test head 10 contains at least one aperture 28 and a vacuum source 87 connected to the test head 10 causes air to be drawn through the web 12 and then through the aperture 28. The test head 10 also includes at least one static port 32 that communicates with the aperture 28. The static port 32 is located very close to the web 12 and measures the static pressure within the aperture 28 before it leaves the aperture 28. A pressure transducer 46 is connected to the static port 32 and provides a measurement of the pressure drop across the web 12. If the volumetric flow rate of air through the web 12 is kept constant, the pressure transducer 46 output 52 is representative of the permeability of the web 12. If the pressure differential across the web 12 is kept constant, measurement of the volumetric flow rate of air through the web 12 will be representative of the permeability of the web 12.

19 Claims, 8 Drawing Figures

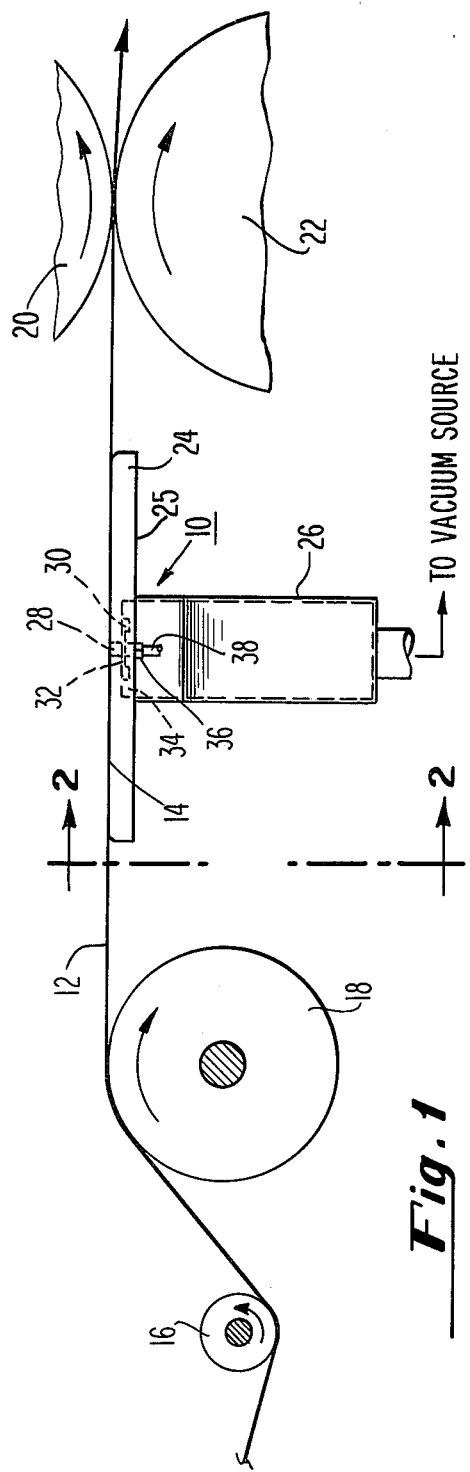
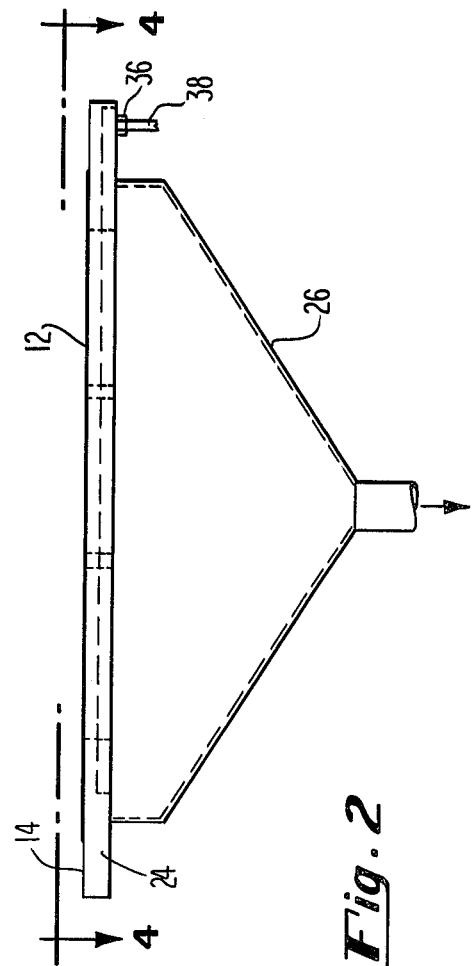

WEB PERMEABILITY TESTER

TECHNICAL FIELD

This invention is directed to an instrument for measuring the permeability of porous sheet materials. The instrument is particularly suitable for continuously measuring the permeability of a traveling web such as a paper web being made by a papermaking machine.

BACKGROUND ART

One apparatus for measuring the permeability of a porous sheet material is described in U.S. Pat. No. 2,861,451, issued Nov. 25, 1958, to N. Emmons. In Emmons, a sample of the porous material is clamped into the tester so that one surface of the material is supported on a perforated planar surface. Air under pressure is caused to flow through the porous material, then through the perforated planar surface, and is then exhausted to the atmosphere after flowing through a tapered, transparent float tube containing an indicating float which positions itself along the tube in accordance with the velocity of air flowing through the tube. The position of the float provides an indication of the permeability of the porous material. The requirement that each sample to be measured must be clamped in the tester makes the apparatus described in the Emmons patent unsuitable for continuously measuring the permeability of a traveling web.

Another instrument capable of measuring the permeability of a sample of a porous web is the Gurley permeability tester. The Gurley permeability tester utilizes a bell or cylinder of aluminum operating in a seal of mineral oil so that as it descends, it forces air through a specially mounted specimen of paper. The volume of air displaced through the specimen is measured by the amount the bell sinks. The usual test consists of determining the time in seconds required to displace 0.0001 cubic meters of air through 0.000645 square meters (1.0 square inch) of paper under a pressure head fixed by the weight and dimensions of the bell. The result obtained, which is inversely related to air permeability, is referred to as the air resistance.

An apparatus capable of continuously measuring the permeability of a moving porous web is described in U.S. Pat. No. 3,371,518, issued Mar. 5, 1968, to M. A. Keyes. In Keyes, the web travels over a hollow, perforated, rotating roll. A stationary suction box within the roll establishes an air pressure differential across the traveling web. In one embodiment, the interior of the suction box is maintained at a predetermined pressure and the flow of air through the suction box is measured and provides an indication of the permeability of the web. In another embodiment, the air flow rate to the suction box is kept constant and the pressure within the suction box is measured to provide an indication of the permeability of the web. One disadvantage of the apparatus described in the Keyes patent is the difficulty of providing a good seal between the rotating roll and the stationary suction box. It is also believed to be a disadvantage to locate the pressure measurement or control point outside of the suction box where it measures pressure changes due to inadequate sealing between the rotating roll and the stationary suction box and due to the expansion of the air as it enters the suction box from the apertures in the rotating roll.

Another apparatus capable of continuously measuring the permeability of a traveling porous web is disclosed in U.S. Pat. No. 3,466,925, issued Sept. 16, 1969, to P. D. Ziegenhagen et al. In that patent, a measuring head is located so that it contacts the moving web. A vacuum is applied to the measuring head which draws air at a constant flow rate through the paper and into the measuring head. The vacuum pressure under the head is measured and provides an indication of the permeability of the web passing across the head. The Ziegenhagen et al. patent also discloses that the measuring head can include a plurality of sealing apertures connected to a vacuum source that is separate from the measurement vacuum source. This sealing section prevents air from flowing under the moving web and into the measuring section of the head.

Both Keyes and Ziegenhagen et al. measure a pressure within the apparatus that includes the pressure differential across the web. In both cases the pressure measurement is taken at a location that is relatively remote from the web, that is, after the air has passed through the apertures of the measurement surface. As a result, the pressure measurement not only measures the pressure changes due to the varying permeability of the web but also the pressure changes due to the expansion of the air as it leaves the apertures of the measuring surface and the pressure changes due to inefficient sealing of the vacuum source, etc. If these latter two parameters are not constant, the pressure measurement will not accurately represent the permeability of the web.

DISCLOSURE OF THE INVENTION

In the permeability tester of this invention, a porous web is placed against a surface of a test head. The test head contains at least one aperture, and a vacuum source connected to the test head causes air to be drawn through the web and then through the aperture. The test head also includes at least one static port that communicates with the aperture. The static port is located very close to the web and measures the static air pressure within the aperture before the air leaves the aperture. A pressure transducer is connected to the static port and provides a measurement of the pressure drop across the web.

In a preferred embodiment of the apparatus, the test head includes an averaging plenum and a static ring, which communicates with the aperture about the entire perimeter of the aperture, and which also communicates with the averaging plenum. The pressure transducer is connected to the plenum thereby providing a measurement of the average pressure drop across the web as measured about the entire perimeter of the aperture.

In one preferred embodiment of the apparatus, the flow of air through the test head is kept constant and the pressure drop across the web is measured to provide an indication of the permeability of the web. In an alternate embodiment of the apparatus, the pressure drop across the web, as indicated by the output of the pressure transducer, is kept constant and the flow rate of air through the sensing head is measured to provide an indication of the permeability of the web.

BRIEF DESCRIPTION OF THE DRAWINGS

While the specification concludes with claims particularly pointing out and distinctly claiming that which is regarded as the present invention, the object and advantages of this invention can be more readily ascertained from the following description of a preferred embodiment when read in conjunction with the accompanying drawings in which:

FIG. 1 is a side elevation of a test head that is used to measure the permeability of a traveling web;

FIG. 2 is a front elevation of the test head as viewed along the line 2—2 of FIG. 1;

BEST MODE FOR CARRYING OUT THE INVENTION

Figure 3:
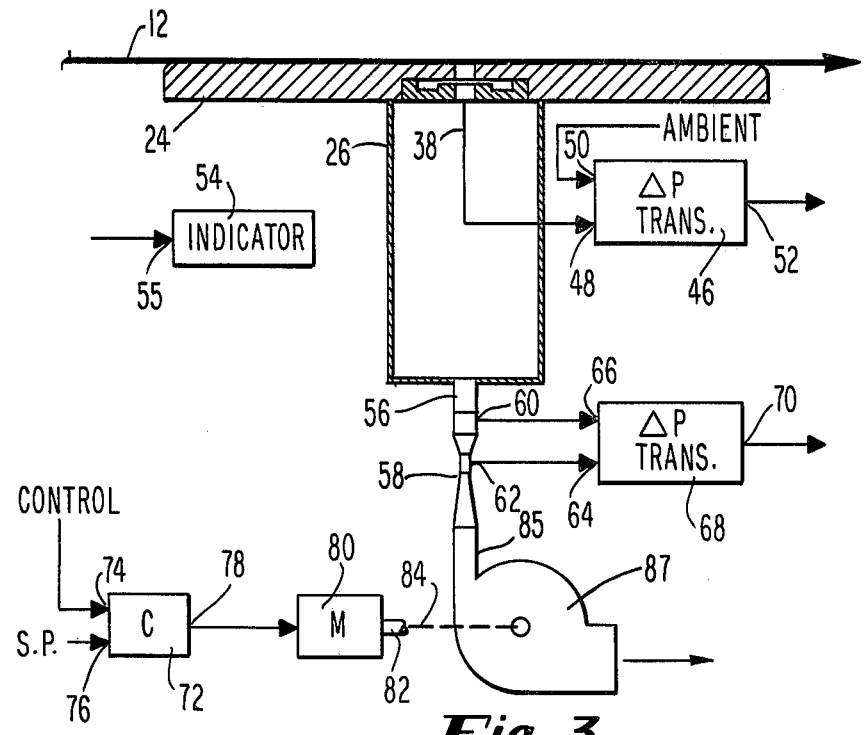
FIG. 3 is a functional block diagram of a web permeability tester.

For the sake of convenience, an element depicted in more than one figure will retain the same element number in each figure. The permeability testing apparatus of this invention can be used to measure the permeability of a stationary web or can provide a continuous measurement of the permeability of a traveling web. As shown in FIG. 1, the test head 10 portion of the permeability tester can be located in a papermaking machine just ahead of calender rolls 20, 22. The test head 10 includes a sensing plate 24 having a test surface 14 that contacts the surface of a traveling paper web 12. The web 12 passes under a guide roll 16 which centers the web in a cross-machine direction, and then passes over a locating roll 18 which locates the elevation of web 12 with respect to test surface 14 so that the web 12 maintains good contact with the measurement surface 14 as the web 12 approaches measurement apertures 28. Similarly, it is important to maintain the elevation of the sensing surface 14 with respect to the nip formed by calender rolls 20, 22 to make sure that the web 12 maintains contact with test surface 14 after the web 12 passes over apertures 28. If the permeability measurement is taken at some other place in the papermaking machine, it may be desirable to include a second locating roll (not shown) for the web 12 after it leaves test head 10. The lower surface 25 of test head 10 is secured to a vacuum box 26. An air tight seal is maintained between lower surface 25 and vacuum box 26 so that all of the air flowing through the vacuum box 26 is air that is pulled through apertures 28.

Figure 4:
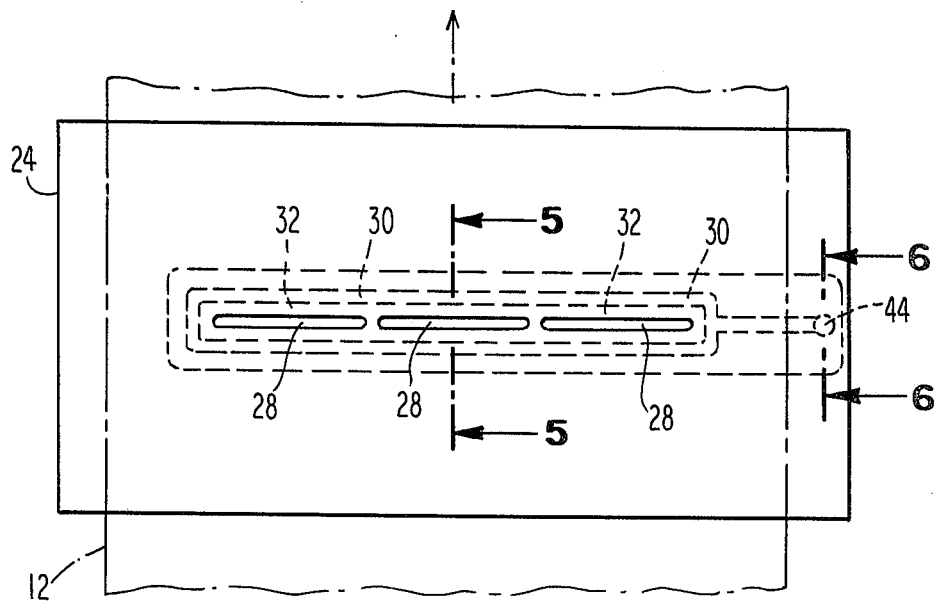
FIG. 4 is a plan view of the test head.
Figure 5:
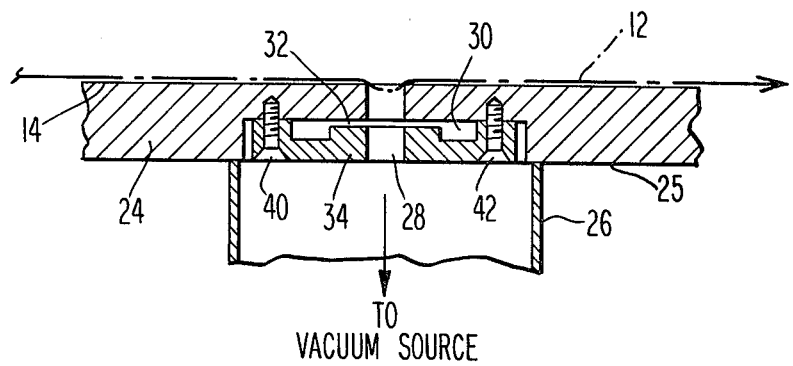
FIG. 5 is a cross-sectional view of the test head taken along the line 5—5 of FIG. 4.
Figure 6:
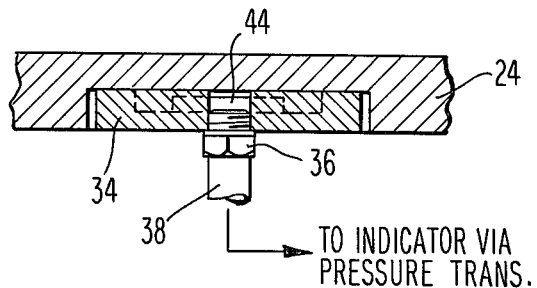
FIG. 6 is a cross-sectional view of the test head taken along the line 6—6 of FIG. 4.

As best shown in FIGS. 4 and 5, the sensing plate 24 includes a plurality of apertures 28 that extend from the test surface 14 to the lower surface 25 of the sensing plate 24. A static ring 32 located within the sensing plate 24 communicates with each aperture 28 about the entire perimeter of each aperture 28. The static ring 32 also communicates with an averaging plenum 30 located within the sensing plate 24. The averaging plenum 30 terminates in a plenum exit port 44 which is best depicted in FIGS. 4 and 6. A portion of plenum exit port 44 adjacent to the lower surface 25 of sensing plate 24 can be threaded to accept a collector fitting 36 which is secured to air tubing 38. The other end of air tubing 38 (not shown) is connected to the input of a pressure transducer (also not shown). As shown in FIGS. 5 and 6, it is preferred to use a two-piece construction to form the static ring 32 and averaging plenum 30 within the test head 10. Thus, a portion of the sensing plate 24 is machined out and an appropriately machined under-assembly 34 is secured to the sensing plate 24 by means of screws 40, 42.

Referring now to FIGS. 4 and 5, in one embodiment of test head 10, the thickness of sensing plate 24 is 0.0127 meters (0.50 inches) thick, and each slot 28 is about 0.00635 meters (0.25 inches) wide and about 0.0762 meters (3.0 inches) long. As depicted in FIG. 4, the cross-sectional dimensions of averaging plenum 30 is about 0.00318 meters (0.125 inches) by 0.00635 meters (0.25 inches). Also, as shown in FIG. 5, the length of the static ring 32 from aperture 28 to plenum 30 is about 0.00635 meters (0.25 inches) and the thickness of the static ring 32 is about 0.000794 meters (0.03125 inches).

Static ring 32 should be located very close to traveling web 12. Two factors limit the location of static ring 32, namely, the structural rigidity of that portion of sensing plate 24 which forms both the measurement surface 14 and the upper side wall of aperture 28, and the fact that the static ring 32 must measure the pressure where there is good air flow in the aperture 28. Thus, as shown in FIG. 4, static ring 32 is located about 0.00635 meters (0.25 inches) below measuring surface 14.

When the test head 10 is used to measure the permeability of a traveling web 12 as shown in the figures, it is preferred that each aperture 28 have the shape of a long, narrow slot wherein the long dimension of the slot is perpendicular to the direction of travel of web 12. Apertures 28 can have other shapes, however, it has been found that, for a given length of the aperture in a direction perpendicular to the direction of travel of web 12, as the dimension of aperture 28 increases in the direction of travel of web 12, (1) the sensitivity of the permeability measurement decreases because the measurement is averaged over a larger area of web 12 over the aperture; (2) the web forms a larger catenary over each aperture 28 which results in increased friction between the edge of the aperture 28 and the web 12 which increases fiber removal from the web; and (3) there is an increased tendency for waves to form in the web as it travels over the apertures 28 of the sensing head 10.

As shown in FIG. 4, the static rings 32 associated with each aperture 28 are connected together to get a pressure differential measurement over substantially the entire width of traveling web 12. It would also be apparent to one skilled in the art that the static ring 32 associated with each aperture 28 could be kept isolated, each being connected to separate differential pressure measurement devices to provide a profile of the permeability of web 12.

Figure 8:
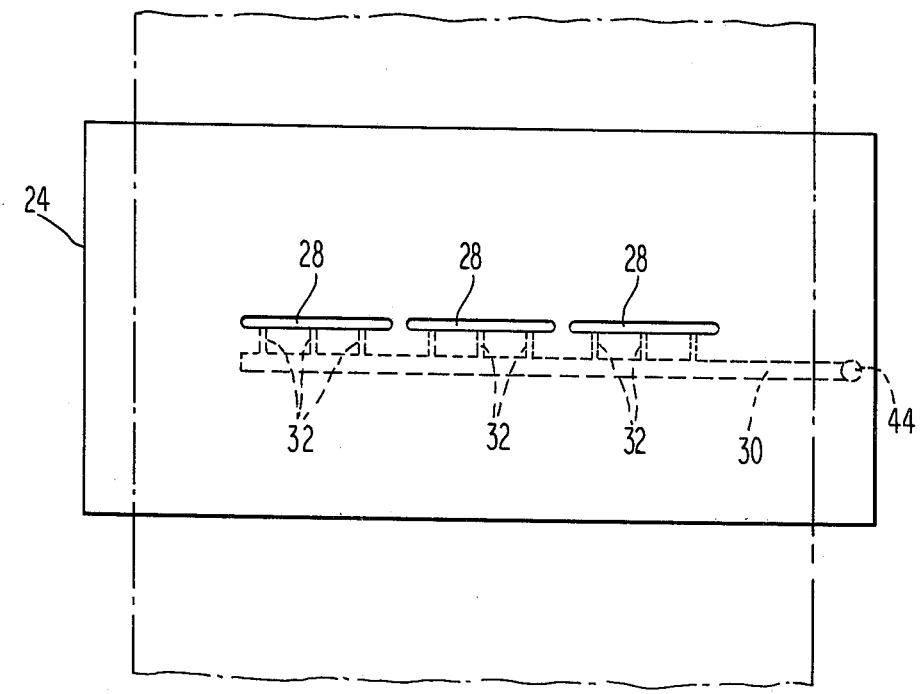
FIG. 8 is a plan view of an alternate embodiment of the test head.

Although the preferred embodiment of test head 10 employs a static ring 32 in communication with the aperture 28 and the averaging plenum 30, an alternate embodiment, depicted in FIG. 8, shows each aperture 28 being connected to averaging plenum 30 by three static ports 32 having a circular cross-section and spaced along the length of aperture 28. It will also be appreciated by those skilled in the art that fewer or more static ports 32 can be employed to connect each aperture 28 to averaging plenum 30. When test head 10 is used to measure the permeability of a fibrous web such as paper, the use of only one or several individual static ports 32 has been found unsatisfactory because loose fibers tend to clog up the static ports 32. The use of a static ring 32, as depicted in FIGS. 4, 5 and 6, has significantly reduced problems caused by fibers clogging up the test head.

FIG. 3 is a block diagram that shows how the test head 10 can be used to provide a continuous indication of the permeability of a web 12 that is traveling over the test surface 14 in the direction shown. The vacuum box 26 has an outlet port 56 which is connected to one end of a venturi 58. The other end of venturi 58 is connected to the inlet port 85 of a suction fan 87 which causes air to be pulled through the porous web 12, through aperture 28, vacuum box 26, outlet port 56, venturi 58, inlet port 85 of exhaust fan 87 where the air is expelled from an exhaust port 89 of suction fan 87. The air tubing 38 is connected to one input 48 of a differential pressure transducer 46. The other input 50 of differential pressure transducer 46 is connected to a reference pressure source which, in most cases, will be the ambient pressure existing just above traveling web 12. The signal appearing at the output 52 of differential pressure transducer 46 is representative of the pressure drop across the traveling web 12. The high pressure static port 60 of venturi 58 is applied to one input 66 of a second differential pressure transducer 68 and the low pressure static port 62 of venturi 58 is applied to the other input 64 of differential pressure transducer 68. The output 70 of differential pressure transducer 68 is a signal that is representative of the volumetric flow rate of air through the web 12 and aperture 28. As represented by dashed line 84, the shaft of suction fan 87 is driven from a shaft 82 of a variable speed DC motor 80. The speed of the motor 80, and therefore the speed of suction fan 87, is controlled from the output 78 of a controller 72. Controller 72 has a first input 76 to which a set point signal is applied either manually by an operator or automatically by a computer. A control signal is applied to the second input 74 of controller 72. An indicator 54 having an input 55 can provide either an analog or a digital indication of the permeability of web 12.

In a preferred embodiment of the permeability tester, the output 52 of differential pressure transducer 46 is applied to the input 55 of indicator 54 and the output 70 of differential pressure transducer 68 is applied to the control input 74 of controller 72. The set point signal applied to the input 76 of controller 78 is adjusted to establish a desired volumetric flow rate of air through web 12 and aperture 28. Controller 78 continually adjusts the speed of suction fan 87 to maintain that constant volumetric flow rate of air through venturi 58, and therefore through the web 12 and aperture 28. Indicator 54 provides a continuous reading of the pressure drop across web 12 which is representative of the permeability of web 12.

The elements depicted in FIG. 3 can be connected in an alternate configuration in order to provide an indication of the permeability of traveling web 12. In this alternate configuration, the output 52 of differential pressure transducer 46 is applied to the control input 74 of controller 72 and the output 70 of differential pressure transducer 68 is applied to the input 55 of indicator 54. The set point signal applied to the input 76 of controller 78 is adjusted to establish a desired pressure drop across web 12. The controller 72 continuously varies the speed of suction fan 87 so as to maintain the pressure drop across the web 12, as measured by differential pressure transducer 46, at the set point value. Indicator 54 provides a reading of the volumetric rate of flow of air through the venturi 58, which is representative of the permeability of web 12.

Figure 7:
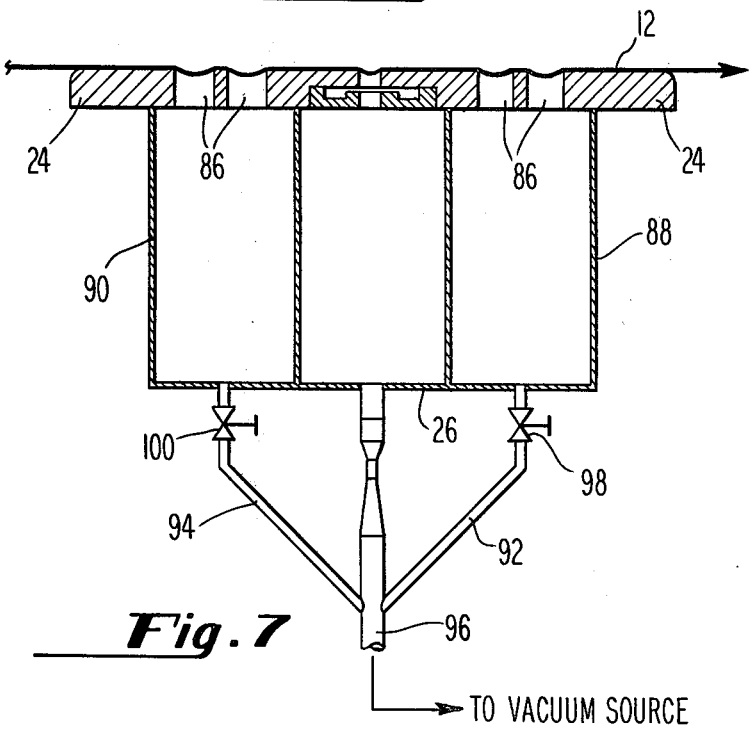
FIG. 7 is a partial side elevation of an alternate embodiment of the test head.

Referring now to FIG. 7, there is shown another embodiment of test head 10. In this embodiment, the web 12 passes over a first set of hold down holes 86 before it passes over aperture 28, and then passes over a second set of hold down holes 86 after it passes over aperture 28. The lower surface 25 of sensing plate 24 is connected to a first hold down vacuum box 90 which is connected to suction fan 87 (not shown) by means of an air pipe 94. The bottom surface 25 of sensing plate 24 is also secured to a second hold down vacuum box 88 which is connected to suction fan 87 by means of an air pipe 92. Air pipes 92 and 94 include control valves 98 and 100, respectively, for controlling the amount of air passing through the web and through the hold down holes 86. These hold down holes 86 are generally not required for soft, lightweight webs such as paper suitable for use as facial tissue or bathroom tissue. Hold down holes 86 may be required for testing certain heavier or stiffer webs. When the hold down holes 86 are used in conjunction with such heavy or stiff webs, it is contemplated that the hold down holes 86 serve two functions. The first function, as described in the aforementioned patent to Ziegenhagen et al. is to hold the web 12 against the measuring surface 14 of the sensing plate 24 so that air does not leak into aperture 28 from beneath the web 12. The second function of the hold down arrangement depicted in FIG. 7 is to control the shape, or catenary, of the web 12 as it passes over aperture 28. For example, if web 12 is a paper web in a papermaking machine, changes in the process conditions could change the catenary of web 12 over aperture 28 which results in changing the area of the web over the aperture 28 which affects the accuracy of the permeability measurement. By adjusting the flow through hold down vacuum boxes 88, 90 the area of the web 12 over the aperture 28 can be controlled thereby compensating for the change in the process and removing the shape of the catenary of web 12 as a variable.

While the present invention has been described with reference to a specific embodiment thereof, it will be obvious to those skilled in the art that various changes and modifications may be made without departing from the invention in its broader aspects. For example, although the sensing head 10 has been depicted as measuring the permeability of a traveling web 12, it will be appreciated by those skilled in the art that the described permeability measuring apparatus can also be used to measure individual samples of a porous material.

What is claimed is:

1. An instrument for measuring the permeability of a web placed against a measuring surface of the instrument comprising:
   (a) a test head containing the measuring surface and having an aperture extending from the measuring surface to a surface of the head not contacted by the web, the test head having at least one static port in communication with the aperture;
   (b) suction means operatively connected to the surface of the head not contacted by the web for causing a constant flow of air through the web then through the aperture; and
   (c) a pressure transducer operatively connected to at least one static port, and responsive to the pressure in the static port and responsive to a reference pressure, for providing a signal representative of the pressure drop across the web, said signal being representative of the permeability of the web.

2. An instrument as recited in claim 1 wherein the test head also has an averaging plenum in communication with at least one static port and wherein the pressure transducer is operatively connected to the averaging plenum.

3. An instrument as recited in claim 1 wherein the static port forms a continuous static ring in communication with the aperture about the entire perimeter of the aperture.

4. An instrument as recited in claim 3 wherein the test head has a plurality of apertures and wherein the static ring communicates with each aperture.

5. An instrument as recited in claim 3 for measuring the permeability of a traveling web wherein the aperture is a slot, the long dimension of the slot being substantially perpendicular to the direction of travel of the web.

6. An instrument as recited in claim 1 wherein the measuring surface includes hold down holes and adjustable suction means operatively connected to the hold down holes for causing air to flow through the web, then through the holes, whereby the web is held against the measuring surface and the catenary of the web over the aperture is controlled.

7. An instrument for measuring the permeability of a web placed against a measuring surface of the instrument comprising:
 (a) a test head containing the measuring surface and having an aperture extending from the measuring surface to a surface of the head not contacted by the web, the test head having at least one static port in communication with the aperture;
 (b) variable suction means operatively connected to the surface of the head not contacted by the web for causing air to flow through the web, then through the aperture;
 (c) a pressure transducer operatively connected to at least one static port, and responsive to the pressure in the static port and to a reference pressure for providing a signal representative of the pressure drop across the web;
 (d) control means, responsive to the pressure transducer signal, for controlling the suction means so as to maintain a constant pressure drop across the web; and
 (e) means, responsive to the flow of air through the aperture, for providing a signal representative of the flow of air through the aperture, said signal also being representative of the permeability of the web.

8. An instrument as recited in claim 7 wherein the test head also has an averaging plenum in communication with at least one static port and wherein the pressure transducer is operatively connected to the averaging plenum.

9. An instrument as recited in claim 7 wherein the static port forms a continuous static ring in communication with the aperture about the entire perimeter of the aperture.

10. An instrument as recited in claim 9 wherein the test head has a plurality of apertures and wherein the static ring communicates with each aperture.

11. An instrument as recited in claim 9 for measuring the permeability of a traveling web wherein the aperture is a slot, the long dimension of the slot being substantially perpendicular to the direction of travel of the web.

12. An instrument as recited in claim 7 wherein the measuring surface includes hold down holes and adjustable suction means operatively connected to the hold down holes for causing air to flow through the web, then through the holes, whereby the web is held against the measuring surface and the catenary of the web over the aperture is controlled.

13. An instrument for measuring the permeability of a web traveling in a machine direction:
 (a) a test head having a measuring surface in contact with the traveling web, the head having at least one aperture extending from the measuring surface to a surface not contacted by the web, the test head having an averaging plenum and a static ring in communication with the averaging plenum and in communication with each aperture about the entire perimeter of each aperture;
 (b) variable suction means, in communication with the aperture, for causing air to flow through the web, then through the aperture;
 (c) flow measurement means, responsive to the flow of air through the aperture for providing a signal representative of the flow of air through the aperture;
 (d) control means, responsive to the flow measurement means signal, for controlling the suction means so as to maintain a constant air flow rate through the web; and
 (e) a pressure transducer operatively connected to the averaging plenum and responsive to the pressure in the plenum and to a reference pressure for providing a signal representative of the pressure drop across the web, said signal also being representative of the permeability of the web.

14. An instrument for measuring the permeability of a web traveling in a machine direction:
 (a) a test head having a measuring surface in contact with the traveling web, the head having at least one aperture extending from the measuring surface to a surface not contacted by the web, the test head having an averaging plenum and a static ring in communication with the averaging plenum and in communication with each aperture about the entire perimeter of each aperture;
 (b) a pressure transducer operatively connected to the averaging plenum and responsive to the pressure in the plenum and to a reference pressure for providing a signal representative of the pressure drop across the web;
 (c) variable suction means, in communication with the aperture, for causing air to flow through the web, then through the aperture;
 (d) control means, responsive to the pressure transducer signal, for controlling the suction means so as to maintain a constant pressure drop across the web; and
 (e) means, responsive to the flow of air through the aperture, for providing a signal representative of the flow of air through the aperture, said signal also being representative of the permeability of the web.

15. A test head for measuring the permeability of a web placed against a measuring surface of the head, said head having an aperture extending from the measuring surface to a surface of the head not contacted by the web, said test head having at least one static port having one end in communication with the aperture, the other end of the static port being adapted to communicate with a pressure measurement device; said surface not contacted by the web being adapted to be connected to a vacuum source for causing air to flow through the web, then through the aperture, whereby the pressure measurement device measures the static pressure drop across the web.

16. A test head as recited in claim 15 also having an averaging plenum in communication with at least one static port said averaging plenum being adapted to communicate with the pressure measurement device.

17. A test head as recited in claim 15 wherein the static port forms a continuous static ring in communication with the aperture about the entire perimeter of the aperture.

18. A test head as recited in claim 17 having plurality of apertures and wherein the static ring communicates with each aperture.

19. A test head as recited in claim 17 for measuring the permeability of a traveling web wherein the aperture is a slot, the long dimension of the slot being substantially perpendicular to the direction of travel of the web.

* * * * *